United States Patent
Kaiser et al.

(10) Patent No.: US 9,958,393 B2
(45) Date of Patent: May 1, 2018

(54) PRINCIPLE COMPONENT ANALYSIS (PCA)-BASED ANALYSIS OF DISCONTINUOUS EMISSION SPECTRA IN MULTICHROMATIC FLOW CYTOMETRY

(75) Inventors: Toralf Kaiser, Birkenwerder (DE); Jenny Kirsch, Berlin (DE); Andreas Gruetzkau, Berlin (DE)

(73) Assignee: DEUTSCHES RHEUMA-FORSCHUNGSZENTRUM BERLIN, Berlin (DE)

( * ) Notice: Subject to any disclaimer, the term of this patent is extended or adjusted under 35 U.S.C. 154(b) by 407 days.

(21) Appl. No.: 13/878,902

(22) PCT Filed: Oct. 12, 2011

(86) PCT No.: PCT/EP2011/005220
§ 371 (c)(1),
(2), (4) Date: Jun. 18, 2013

(87) PCT Pub. No.: WO2012/048906
PCT Pub. Date: Apr. 19, 2012

(65) Prior Publication Data
US 2013/0266959 A1  Oct. 10, 2013

Related U.S. Application Data

(60) Provisional application No. 61/392,439, filed on Oct. 12, 2010.

(30) Foreign Application Priority Data

Oct. 12, 2010  (EP) .................................. 10013552

(51) Int. Cl.
*G01N 21/64* (2006.01)
*G01N 15/14* (2006.01)
(Continued)

(52) U.S. Cl.
CPC ....... *G01N 21/6486* (2013.01); *G01N 15/147* (2013.01); *G01N 15/1429* (2013.01);
(Continued)

(58) Field of Classification Search
CPC ............... G01N 21/6486; G01N 15/14; G01B 2015/1037
See application file for complete search history.

(56) References Cited

U.S. PATENT DOCUMENTS 4,727,020 A * 2/1988 Recktenwald ..... G01N 33/5094
356/39
5,102,625 A * 4/1992 Milo ...................... C09K 11/06
250/227.21

(Continued)

OTHER PUBLICATIONS https://www.rp-photonics.com/optical_filters.html, obtained using Wayback Machine with a date of Feb. 5, 2009.*
(Continued)

*Primary Examiner* — Jill A Warden
*Assistant Examiner* — Matthew D Krcha
(74) *Attorney, Agent, or Firm* — Agris & Von Natzmer, LLP; Joyce Von Natzmer

(57) ABSTRACT

The invention relates to a system for acquiring discontinuous emission spectra data, whereby the data is analyzed by a multivariate statistic model or equivalent model, such as principal component analysis and the use of the system for flow cytometry.

13 Claims, 6 Drawing Sheets

Figure 1:
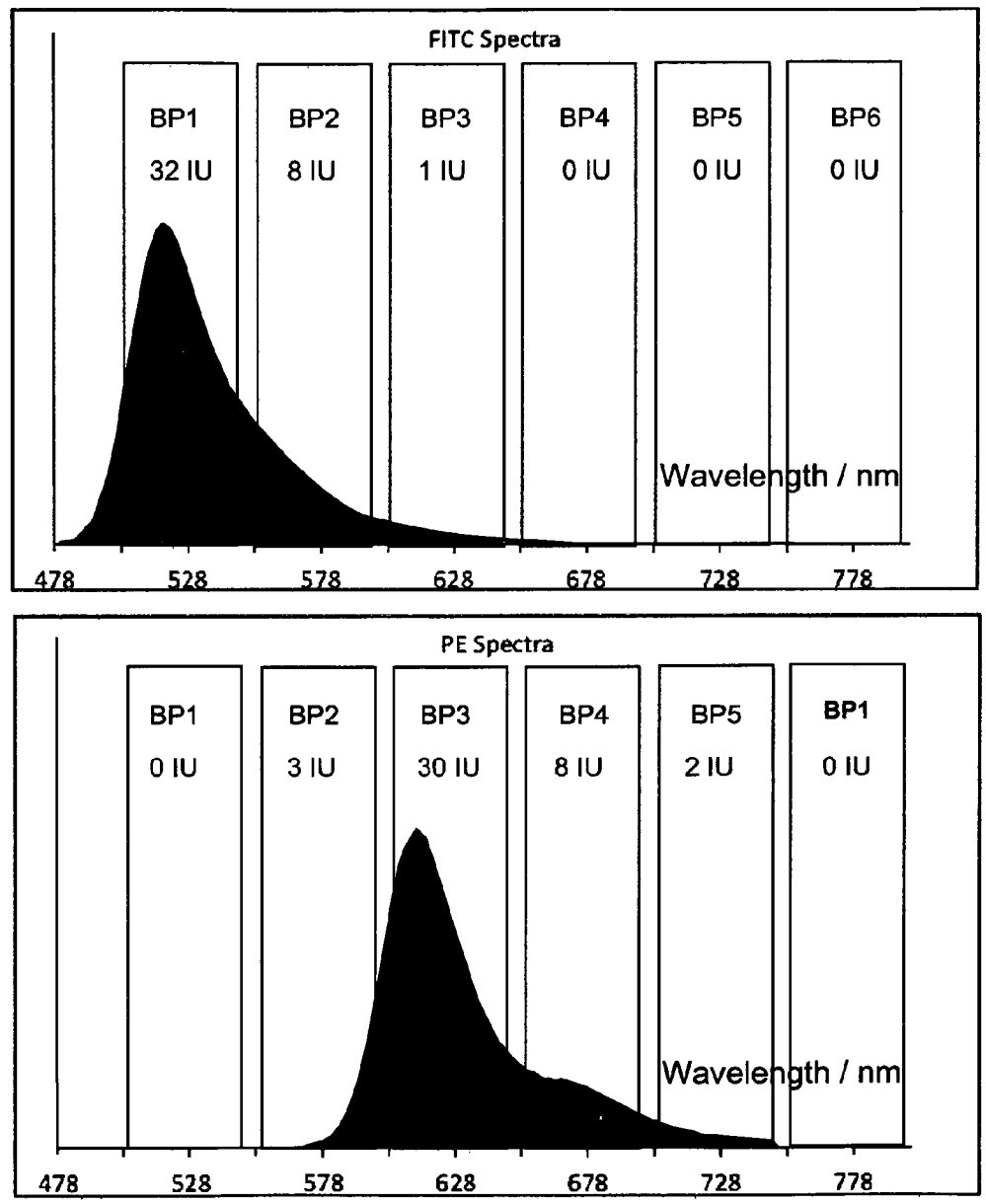
Figure 1:
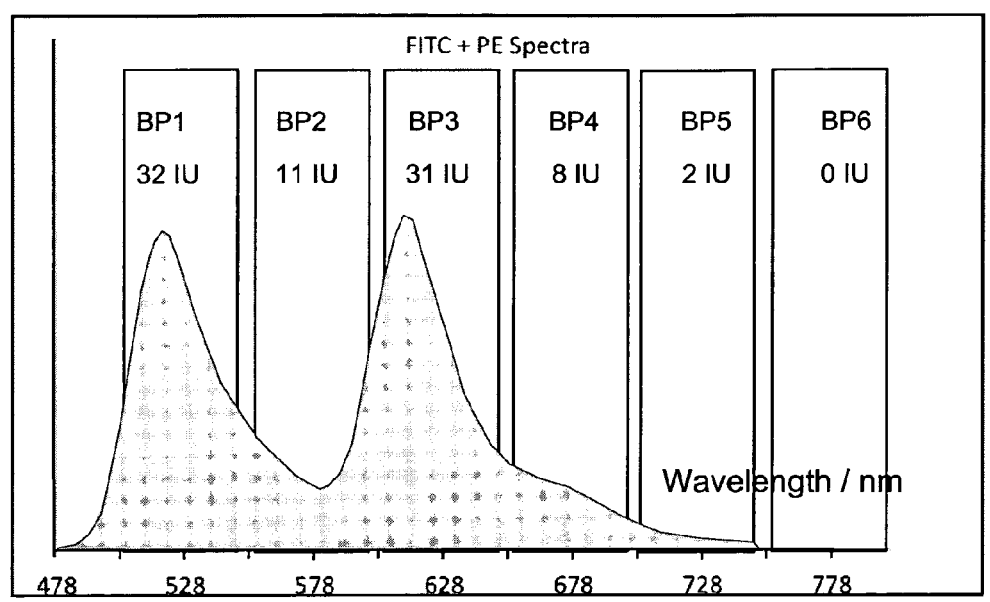

(51) Int. Cl.
*G01N 15/00* (2006.01)
*G01N 15/10* (2006.01)

(52) U.S. Cl.
CPC ... *G01N 15/1459* (2013.01); *G01N 2015/008* (2013.01); *G01N 2015/0073* (2013.01); *G01N 2015/0084* (2013.01); *G01N 2015/1006* (2013.01); *G01N 2015/1488* (2013.01); *G01N 2015/1497* (2013.01); *G01N 2021/6421* (2013.01); *G01N 2021/6423* (2013.01); *G01N 2201/1293* (2013.01)

(56) References Cited

U.S. PATENT DOCUMENTS

| | | | |
|---|---|---|---|
| 6,091,843 | A | 7/2000 | Horesh et al. |
| 6,246,479 | B1* | 6/2001 | Jung ............ G01J 3/02 250/226 |
| 6,592,822 | B1 | 7/2003 | Chandler |
| 6,942,773 | B1* | 9/2005 | Olivares ............ G01N 15/1463 204/452 |
| 2002/0097388 | A1* | 7/2002 | Raz ............ 356/39 |
| 2003/0139886 | A1 | 7/2003 | Bodzin et al. |
| 2003/0215892 | A1 | 11/2003 | Orfao De Matos Correia E Valle |
| 2004/0025602 | A1* | 2/2004 | Norton ............ G01N 15/1459 73/863.21 |
| 2004/0207731 | A1* | 10/2004 | Bearman ............ G01N 15/1463 348/207.99 |
| 2005/0030534 | A1* | 2/2005 | Oldham ............ B82Y 10/00 356/344 |
| 2005/0207633 | A1 | 9/2005 | Arini et al. |
| 2005/0275839 | A1 | 12/2005 | Robinson et al. |
| 2006/0087651 | A1* | 4/2006 | Montaser ............ G01N 15/065 250/288 |
| 2006/0265150 | A1* | 11/2006 | Hu ............ G01N 27/026 702/50 |
| 2010/0155577 | A1 | 6/2010 | Kesel et al. |

OTHER PUBLICATIONS https://www.thermofisher.com/us/en/home/references/molecular-probes-the-handbook/technical-notes-and-product-highlights/selecting-optical-filters-for-fluorescence-microscopy.html. No Date.*
K. M. Carter, R. Raich, W. G. Finn and A. O. Hero, "Information Preserving Component Analysis: Data Projections for Flow Cytometry Analysis," in IEEE Journal of Selected Topics in Signal Processing, vol. 3, No. 1, pp. 148-158, Feb. 2009.*
Watson, D. et al., A Flow Cytometer for the Measurement of Raman Spectra, Cytometry Part A, 2008, International Society for Analytical Cytology, 73A, pp. 119-128.
Robinson, J., Multispectral Cytometry: The Next Generation, Flow Cytometry, Biophotonics International, Oct. 2004, pp. 36-40.

* cited by examiner flow cytometric system

PRINCIPLE COMPONENT ANALYSIS (PCA)-BASED ANALYSIS OF DISCONTINUOUS EMISSION SPECTRA IN MULTICHROMATIC FLOW CYTOMETRY

CROSS-REFERENCE TO RELATED APPLICATIONS

This is the U.S. national stage of International application PCT/EP2011/005220, filed Oct. 12, 2011 designating the United States and claiming the benefit of U.S. provisional patent 61/392,439, filed Oct. 12, 2010 and priority from European patent application EP 10013552.4, filed Oct. 12, 2010.

DESCRIPTION

The invention relates to a system for acquiring discontinuous emission spectra data, whereby the data is analyzed by a multivariate statistic model or equivalent model, such as principal component analysis and the use of the system for flow cytometry. The invention also relates to a method for detecting biological particles of interest from a sample comprising moving particles from a sample of unknown biological particles in a fluid flow stream or in a lab-on-a-chip; providing an incident beam of illumination directed at the particles in said flow stream; detecting light-related data associated with each moving particle as the particle passes through said beam of illumination; storing data of particles having common characteristics based on light data collected from such particles; whereby the light detected is divided into distinct wavelengths bands and the data is analyzed by principal component analysis.

BACKGROUND OF THE INVENTION

Cytometers are known in the art that are equipped with up to 7 lasers, which will allow the detection of up to 49 parameters. Independent of these impressive hardware developments, the detection is still based on fluorochromes and is therefore restricted by the need of optical bandpass filters collecting only a small, but characteristic part of a particular emission spectrum. As a consequence, limitations arise in the sensitivity and resolution of partially overlapping fluorescence signals. Moreover, analysis of those high-dimensional datasets, especially in a non-hypothesis driven manner, will be a challenge of future software developments.

Flow cytometry describes a technique where a beam of light (usually laser light) of a single wavelength is directed onto a hydrodynamically-focused stream of fluid. Flow cytometers are frequently used for the analysis of particles such as biological cells or beads in a number of different applications. Such systems allow for determination of both particle morphology and evaluation of particle features by detection of optical labels. The ability to distinguish multiple particles sizes and colors allows multiplex application providing higher capacity of this technology to obtain information from analyzed targets.

The term "particle" as used herein means any discrete target that may be optically analyzed, enumerated or sorted by a flow cytometer. The particles of the present invention include cells, cell fragments and beads. In flow cytometer systems liquid containing target particles are fed from a container into a flow cell. The flow cells separate particles into a stream of individual particles that flow past a detection location. The particles may flow as individual droplets, but to reduce optical noise from refraction it is often preferred to have the particle stream flow through a cuvette where particles in the flow stream are analyzed. At the detection location a beam of focused illumination light (often a laser beam) illuminates the passing particles. Light scattered by the passing particles is detected by forward and side scatter detectors allowing determination of particle morphology. Light emitted from particles is collected and transmitted to detection optics. The particle (generally a cell or bead) may be labelled with one or more dyes having a characteristic excitation and fluorescent emission wavelength. The dye may be conjugated to a binding agent (e.g. a monoclonal antibody) allowing targeting of specific antigen associated with the bead or cell.

Each suspended particle (from especially 0.2 to 150 micrometers) passing through the beam scatters the ray, and fluorescent chemicals found in the particle or attached to the particle may be excited into emitting light at a longer wavelength than the light source. Light beam splitters separate the collected light into component wavelengths. These beams are directed through a bandpass filter to a light detector (e.g. photomultiplier tube). A specific wavelength associated with each dye is individually detected by at least one detector. The combination of scattered and fluorescent light is picked up by the detectors, and, by analysing fluctuations in brightness at each detector (one for each fluorescent emission peak), it is then possible to derive various types of information about the physical and chemical structure of each individual particle. Forward scatter (FSC) correlates especially with the cell volume and side scatter (SSC) depends on the inner complexity of the particle (i.e., shape of the nucleus, the amount and type of cytoplasmic granules or the membrane roughness). Some flow cytometers on the market have eliminated the need for fluorescence and use only light scatter for measurement. Other flow cytometers form images of each cell's fluorescence, scattered light, and transmitted light.

The data generated by flow-cytometers can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols exist for diagnostic and clinical purposes especially in relation to hematology.

The plots are often made on logarithmic scales. Because different fluorescent dyes' emission spectra overlap, signals at the detectors have to be compensated electronically as well as computationally. Data accumulated using the flow cytometer can be analyzed using software, e.g., WinMDI (deprecated), Flowjo, or CellQuest Pro. Once the data is collected, there is no need to stay connected to the flow cytometer. For this reason, analysis is most often done on a separate computer. This is especially necessary in core facilities where usage of these machines is in high demand.

Recent progress on automated population identification using computational methods has offered an alternative to traditional gating strategies. Automated identification systems could potentially help findings of rare and hidden populations. Representative automated methods include FLOCK in Immunology Database and Analysis Portal (ImmPort), FLAME in GenePattern and flowClust in Bioconductor. Collaborative efforts have resulted in an open project called FlowCAP (Flow Cytometry: Critical Assessment of Population Identification Methods) to provide an objective way to compare and evaluate the flow cytometry data clustering methods, and also to establish guidance about appropriate use and application of these methods.

In a conventional flow cytometer a combination of optical filters and dichroics is used in order to detect a specific fluorescence emission range of a single dye. In a multicolour experiment the spill over needs to be compensated and it has to be carefully analysed by sequential gating strategies. Therefore, actually multi-dimensional experiments, are still a time-consuming procedure including cytometer setup, sample collection and manual data analysis. Moreover, multidimensionality is restricted by the availability of appropriate fluorochromes that can be combined according to their unique emission spectra characteristics.

SUMMARY OF THE INVENTION

It was an objective of the invention to provide a method and system which overcomes the problems known in the state of art. In light of the prior art, the technical problem underlying the present invention is to provide an improved or alternative method or system for acquiring emission spectra data.

This problem is solved by the features of the independent claims. Preferred embodiments of the present invention are provided by the dependent claims.

Therefore, an object of the invention is to provide a system for acquiring discontinuous emission spectra data, whereby the data is analyzed by a multivariate statistic model or equivalent model, such as principal component analysis.

The multivariate statistic model comprises multivariate analysis of variance, multivariate regression analysis, factor analysis, canonical correlation analysis, redundancy analysis, correspondence analysis, multidimensional scaling, discriminant function, linear discriminant analysis, clustering systems, recursive partitioning, principal component analysis, non-linear principle component analysis, information preserving component analysis (IPCA) and/or artificial neural networks, preferably principal component analysis and/or non-linear principle component analysis.

The principal component analysis can also be termed PCA. The person skilled in the arts knows that PCA is a model of multivariate statistics, which describes a form of statistics encompassing the simultaneous observation and analysis of more than one statistical variable.

The discontinuous emission spectrum is preferably achieved by optical bandpass filters, optical gratings, optical grids and/or optical prisms. In a preferred embodiment, the optical bandpass filters divide the emission spectrum into at least two to ten separate wavelength bands, for example, 2, 3, 4, 5, 6, 7, 8, 9 or 10 bands. However, it could also be preferred that the spectrum is divided into less or more distinct bands. It is preferred that the system is used for flow cytometry.

In one embodiment the system as described herein is characterised in that fluorochromes are used to identify particles, whereby the fluorochromes are excited by a laser or LED.

The invention also concerns a flow cytometry apparatus comprising the system, which preferably allows the acquiring of data without the need of gating. The flow cytometry apparatus is preferably a standard cytometer which can be used as a multispectral cytometer due to the system.

The invention also provides a method for detecting biological particles of interest from a sample comprising:
 a. moving particles from a sample of unknown biological particles in a fluid flow stream or in a lab-on-a-chip;
 b. providing an incident beam of illumination directed at the particles in said flow stream;
 c. detecting light-related data associated with each moving particle as the particle passes through said beam of illumination;
 d. storing data of particles having common characteristics based on light data collected from such particles;
whereby the light detected is divided into distinct wavelengths bands and the data is analyzed by principal component analysis.

The sample is preferably a fluid comprising a biological particle. The particles to be detected are preferably cells, comprising eukaryotic or prokaryotic cells.

The term "lab-on-a-chip" (LOC) refers to a device that integrates one or several laboratory functions on a single chip, preferably of only a few millimetres to a few square centimetres in size. LOCs deal with the handling of extremely small fluid volumes down to less than picoliters.

It is preferred that said detecting step includes detecting a plurality of different light signals. Furthermore it is preferred that said detecting step includes detecting light scatter and fluorescence signals simultaneously.

In another preferred embodiment, the said detecting step includes detecting light scattered in at least two different directions and detecting fluorescence emitted by particles at a minimum of two different wavelengths. It is also preferred that the light detected is divided in at least two to ten different wavelength bands.

In one embodiment the method as described herein is characterised in that said detecting step includes detecting scattered light in a multiplexing serial manner.

In another embodiment the method as described herein is characterised in that the light is detected by Photomultiplier, Multi-Channel-Photomultiplier, CCD-Camera or Photodiodes.

Preferably, the principal component analysis algorithm is implemented in a standard flow cytometry software. The analysis of data is simplified by implementing the principal component analysis algorithm in a software, which is commonly used to analyze the data generated by flow cytometry. It can also be preferred that a probability binning algorithm is also implemented either in the software or the system.

It was very surprising, that the principal component analysis can be used for analyzing a discontinuous emission spectrum. The spectrum can for example be generated by a fluorochrome or a fluorophore, which is attached to an antibody or bead and analyzed by a flow cytometry apparatus. The principal component analysis can be used for normalization and population classification.

A further aspect of the invention relates to the use of principal component analysis as described herein, wherein the emission spectrum is emitted by fluorochromes with similar emission spectra.

The invention also relates to a kit for analyzing biological particles by flow cytometry, wherein the kit uses a system described herein. In a preferred embodiment the at least one component of the kit is determined by the method as described above.

A further aspect of the invention relates to a computational program for analyzing a biological particle, preferably by flow cytometry, comprising a multivariate statistic model or equivalent model, preferably a principal component analysis.

The invention describes an adaption of a multi-spectral imaging approach to flow cytometry to have potential new opportunities for the combination of fluorochromes, which cannot be separated by a conventional filter setup. This technology captures images at distinct (for example 3 to 7) wavelengths intervals, which can be used for spectral decomposition of full colour images by the method of principal component analysis (PCA) (ref. 1).

The present invention represents a significant and unexpected improvement over those systems and methods used in the prior art. It was until now unknown that discontinuous emission spectra data could be collected and analysed in the context of flow cytometry, whereby the data is analyzed by a multivariate statistic model or equivalent model, such as principal component analysis.

One surprising advantage of the system of the present invention is that a standard cytometer can be used for the data collection and PCA according to the present invention just by changing the optical filters, thereby providing a multispectral cytometer. No further expensive modifications as described in the literature are required (ref. 4, 5), therefore providing a cost-effective and practical method for improving the data acquisition and quality of data acquired on existing flow cytometry devices.

Furthermore, the present system and method enables the analysis and representation of multiplex data in a more efficient and effective manner, for example whereby the frequency of monocyte and lymphocyte subsets within PBMCs are classified through PCA analysis, the invention provides a comparable statistical distribution to the known standard method, but enables representation of subsets in one dot plot without compensation.

Lack of Compensation of Overlapping Fluorescence Portions

When using the system of the present invention the compensation of overlapping fluorescence portions is unnecessary, because the assignment of the biological parameter (antibody) to the physical parameter (fluorochromes) is enabled via the principle component analysis. No masking or removal of spectral ranges is carried out, but rather an almost gapless detection of the emission spectra is achieved. Through this feature an increased sensitivity of the flow cytometer is achieved. Through the absence of compensation steps the material and cost required for immuno-phenotyping is reduced to the minimum. The subjective pre-processing of the measurement data by the user is subsequently omitted and the number of incorrect analyses is dramatically reduced.

Visualisation of Measurement Parameters

The representation of the measurement data can be reduced to a single dot plot independent of the number of measured parameters. With the reduced data achieved through the principle component analysis and the defined principle components, all biological parameters can be described in two dimensions. The result of this is a strongly reduced time cost for the user and additionally the visual requirements of the user and the software are reduced to the minimum. The representation of the measurement data is free from subjective influences and is therefore objective— ultimately avoiding distortion of the data collection and analysis by biological hypothesis or individual tendencies of the user.

Gating of Cell Samples

Sequential gating can be omitted in the present invention because only a single dot plot is required for visualisation. The manual positioning of the gates is omitted and subjective data distortion is thereby significantly reduced. This enables the analysis of measurement data in a high throughput method with a pre-defined gating strategy. The effort required for the analysis of a patient sample is minimal, for example analysis of 10 measurement parameters for the determination of an immune status can be carried out within a few hours, which was previously only able to be carried out over a number of days.

Reproducibility of the Measurements

Flow cytometers with multiple lasers are (with regard to the hardware components) severely susceptible to faults or breakdowns and generally run in an unstable manner. With assistance of the multispectral analysis it is possible to use only one laser to excite the fluorochromes and also to use fluorochromes with strongly overlapping spectra. From this increased device stability is achieved, due to reduced components and a reduced number of necessary measurement series. The stability of the system and flow cytometer is an essential factor for clinical applications, for experiments with patient samples, for tests running over long periods of time (such as high throughput analyses or screens) or for multi-centric studies.

User Friendliness

The present invention enables flow cytometry analysis with stably integrated structural optical elements and a reduced number of lasers. While commercially available flow cytometers presently exhibit a side length of 1.60 m and a weight of approx. 200 kg, and comprise at least 3 lasers and the corresponding structural optical elements, the present invention provides the possibility for cytometers to be reduced in size by half (or more) and to exhibit improved functionality and flexibility in their application. The present invention enables, in addition to the optical filter settings, flow cytometers with permanently installed device settings. Through this feature untrained users can obtain objective and meaningful data. High-cost maintenance contracts with producer companies are also subsequently reduced, providing a significant cost reduction over presently known systems.

FIGURES

FIG. 1 Shows the emission spectra of FITC, PE and PE+FITC, which are mapped by a combination of 6 different band pass filters (BP). Single fluorophores and combinations were defined by a unique fingerprint. IU (integrated unit) quantifies the area under the curve which defines the specific energy of the fluorophores per BP.

Figure 2:
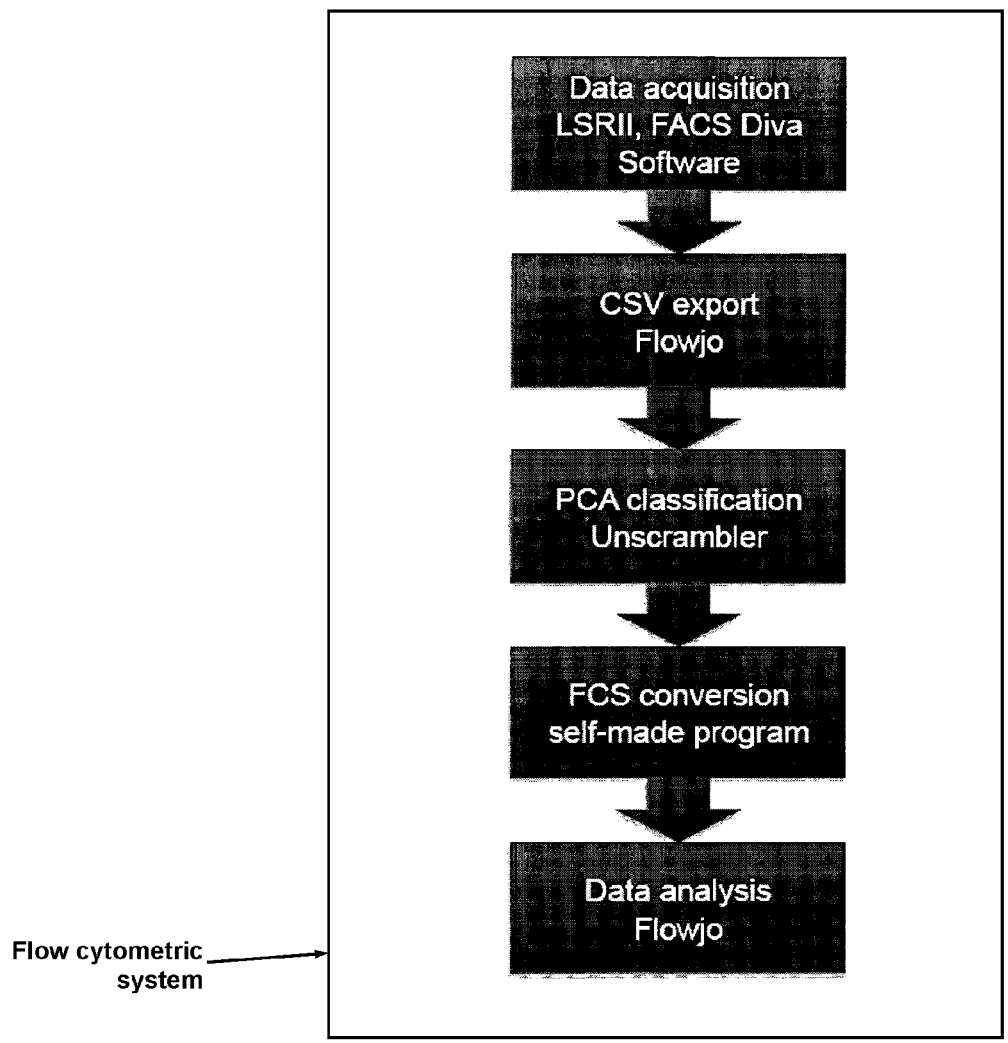

FIG. 2 Overview of data processing

Figure 3:
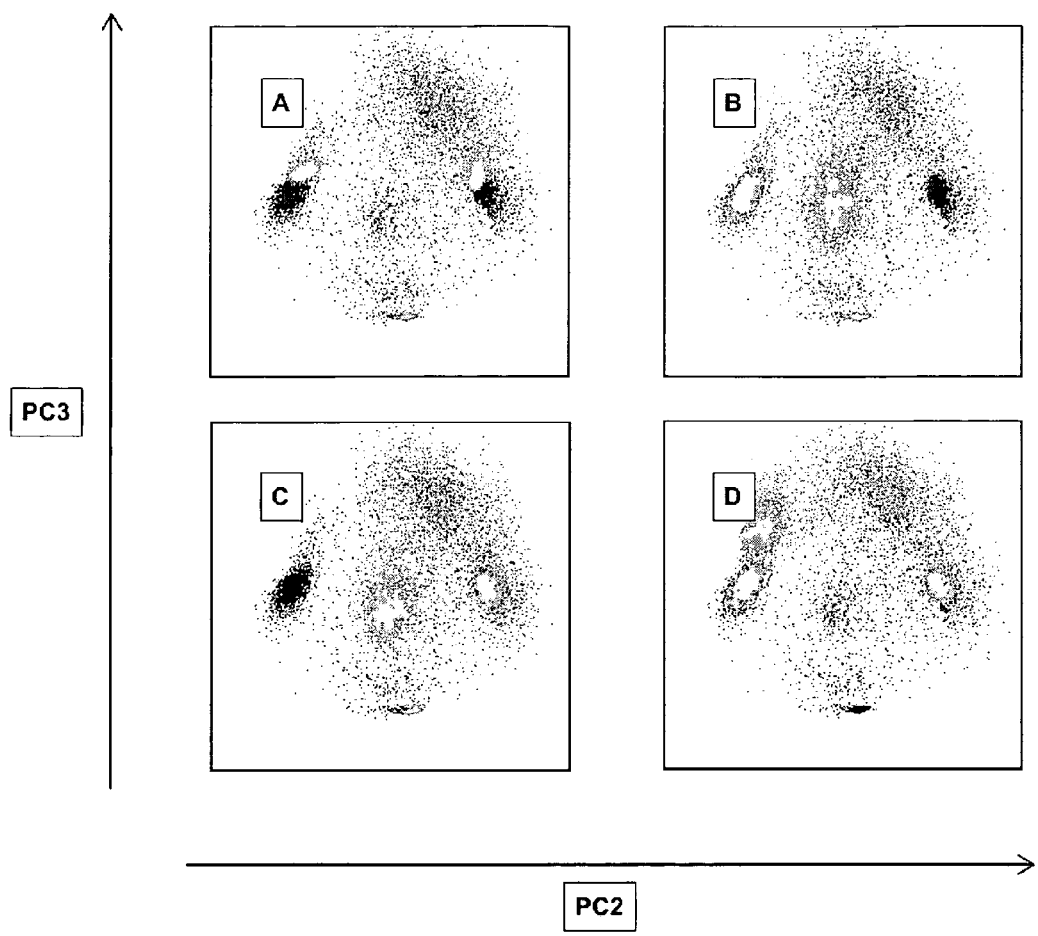

FIG. 3 Shows an overlay of FMO-controls (light grey) and complete stained cells (black): (A) FMO CD3, (B) FMO CD8, (C) FMO CD4, (D) FMO CD14. All plots are calculated by PCA.

Figure 4:
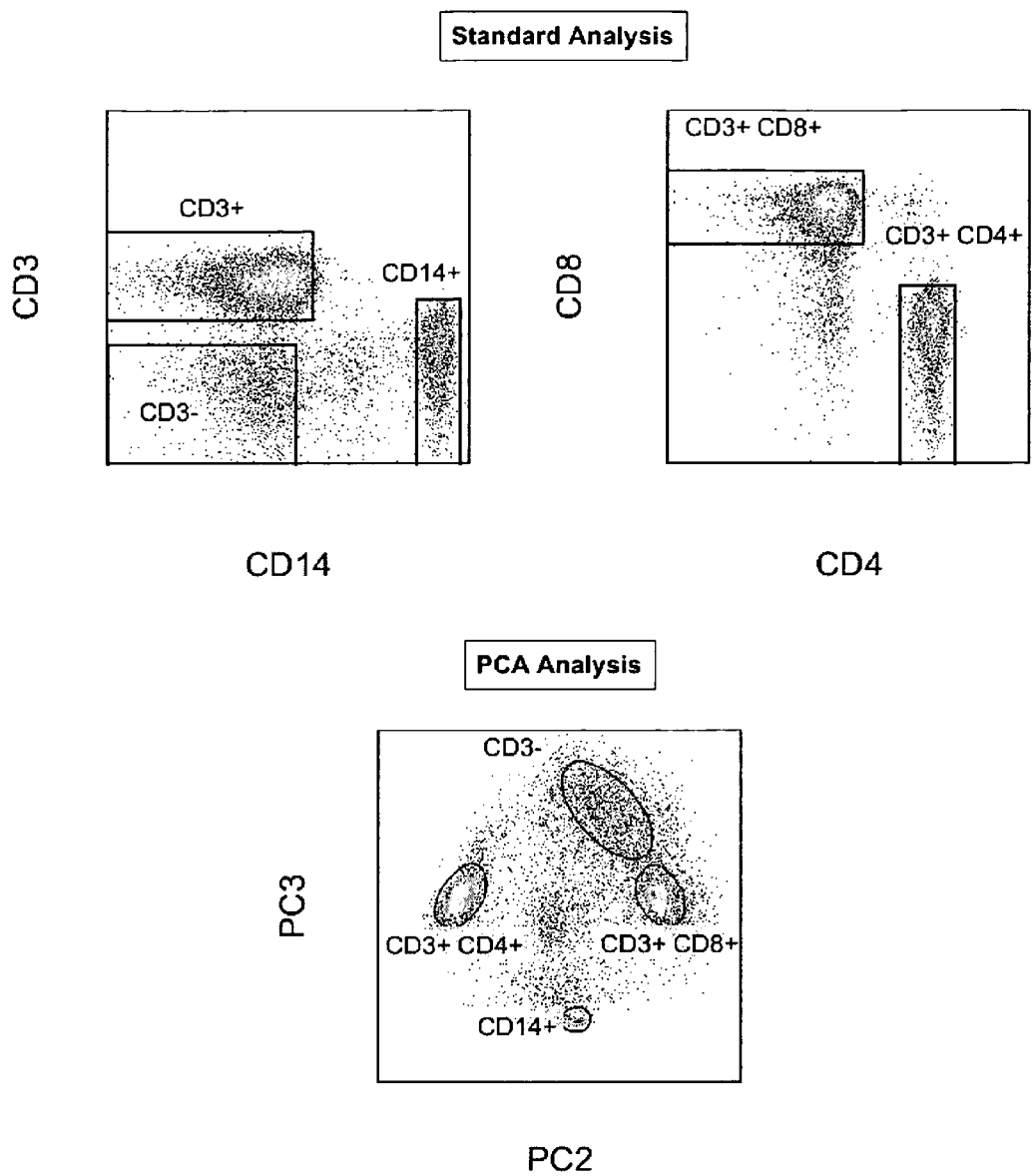

FIG. 4 Shows the result of the standard analysis and the PCA analysis of the present invention. On top standard analysis is depicted and sequential gating of CD4/CD8populations are shown. Figure below: Only one dotplot required to classify all subsets by PCA.

Figure 5:
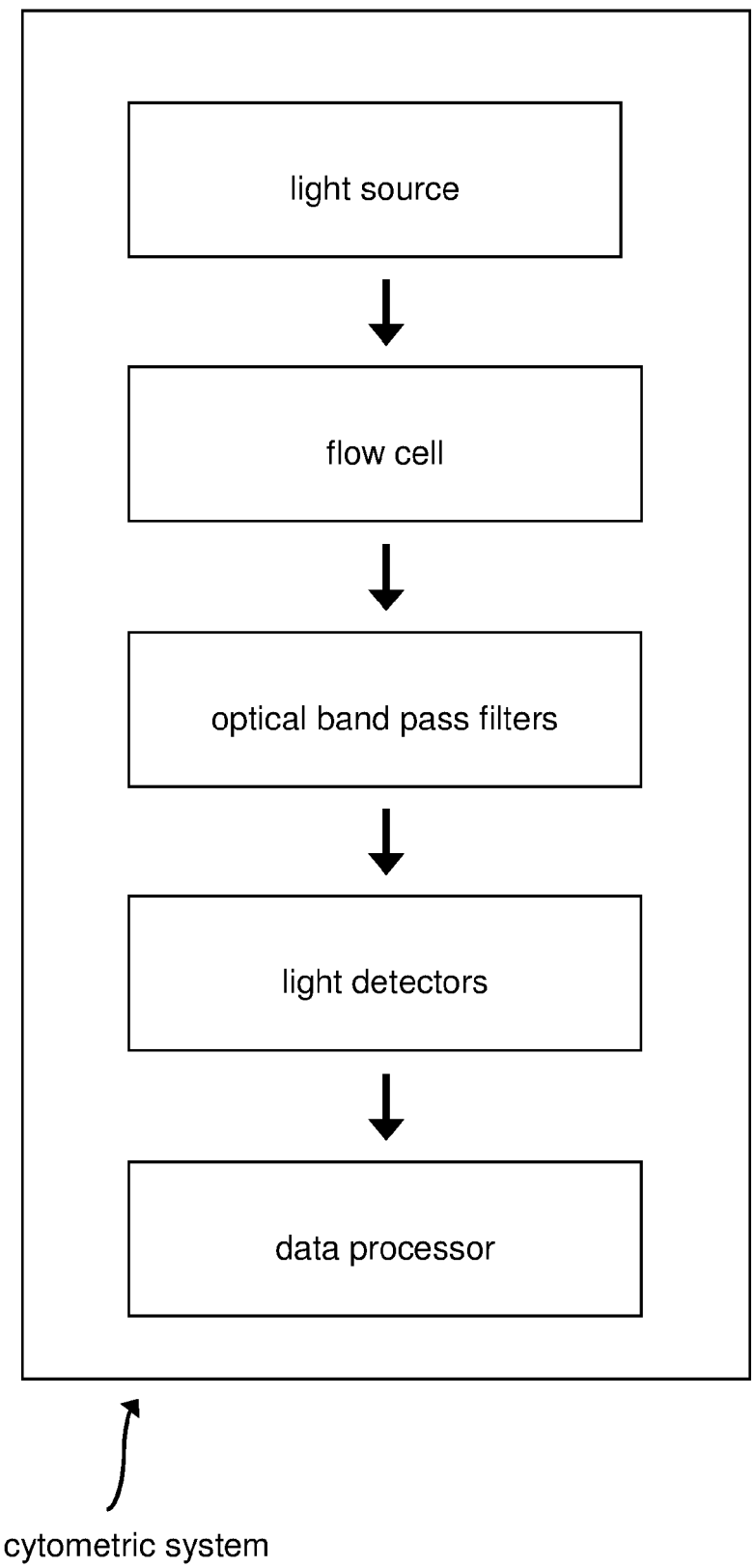

FIG. 5 Shows an overview of the relationship of the elements of the flow cytometric system, in particular the light source, the flow cell, the optical bandpass filters, the detectors and indicates how the light is passed through the system from the light source to the detectors and to the processor(FIG. 2).

DETAILED DESCRIPTION OF THE INVENTION AND EXAMPLES

The invention describes a system, in which discontinuous emission spectra is acquired and analyzed by principal component analysis (PCA). In a proof-of-principle study it was shown that the simultaneous detection of up to 4 fluorochromes, which were all excited by a 488 nm Argon-laser could be resolved by the detection of a discontinuous emission spectrum. In other words a standard cytometer was used just by changing the optical filters as a multispectral cytometer. No further expensive modifications as described in the literature are required (ref. 4, 5). For simplifying data processing, PCA algorithms have to be implemented in standard flow cytometry software.

The invention enables new possibilities in combining fluorochromes with similar emission spectra for the first time. For a complete unsupervised analysis of multi-chromatic flow cytometry data, additional tools, such as the Probability Binning algorithm (ref. 6) are preferably implemented, which finally will help to exploit new dimensions in multiparametric flow cytometry. Further studies in progress show that it is possible to detect up to 10 fluorochromes with 6 PMT's excited by one laser.

The detection principle was applied to a conventional flow cytometer by using optical bandpass filters (BP) to divide the emission spectrum between 505 and 795 nm into six separate wavelength bands. This instrumental alignment and the application of PCA were used to detect the spectral fingerprints of each fluorochromes combination. The detection principle is shown in FIG. 1. In a proof-of-principle study a blue laser for the excitation of 4 fluorochromes was used, which were conjugated to lineage specific antibodies to identify main leukocyte populations in peripheral blood samples.

Human PBMC were stained on ice for 15 min with fluorescent-conjugated antibodies (CD14 PE-Alexa Fluor 700, CD8 PE-Cy7, CD4 FITC and CD3 PerCp) and then washed two times with PBS/BSA. In addition, FMO-controls (Fluorescence Minus One) were prepared to identify cell subsets inside the PCAplots (ref. 2). All data were collected (20.000 events each sample) on a LSRII (BD, San Jose, Calif.) with four fixed-alignment 355 nm, 405 nm, 488 nm and 633 nm lasers and two different filter-settings as shown in Table 1. All lasers were switched off with the exception of the 488 nm laser to minimize background noise.

TABLE 1

Filter configurations of the cytometer LSRII. All filters were installed in the octagon which is connected to the 488 nm laser

| PMT | PCA setup | | Standard setup | |
|---|---|---|---|---|
| | Beam-splitter | Bandpass | Beam-splitter | Bandpass |
| A | 750LP | 775/40 | 735LP | 780/60 |
| B | 700LP | 725/50 | 690LP | 720/30 |
| E | 650LP | 675/40 | 650LP | 670/30 |
| D | 600LP | 625/40 | 550LP | 575/26 |
| E | 550LP | 575/40 | 505LP | 520/30 |
| F | | 525/40 | | 488/10 |

After determining the min PMT voltage, primary FCS-files were acquired by FACSDiva software (BD, version 6.1.3) and exported via FlowJo (Tree Star, USA, version 7.1) into CSV-format. Unscrambler (Camo, Norway, version 9.8) was used for normalization and population classification by PCA. PCA files are not compatible to cytometry data format. Therefore, a custom-made program (written in C#) was used to convert Unscrambler results into FCS 3.0 format (FIG. 2). Dotplots in FIG. 3 illustrates the cell subset identification strategy via FMO/complete staining overlay and PCA analysis.

In order to compare the quantity and quality of the PCA approach to standard analysis the identical samples were measured by using the recommended filter setting (Table 1), compensation and sequential gating strategy as shown in standard analysis (FIG. 4). Table 2 illustrates the frequency of monocyte and lymphocyte subsets within PBMCs classified through PCA and standard analysis. Both setups show comparable statistical distributions. Data compression by PCA allows representation of subsets in one dot plot without compensation.

TABLE 2

Comparison of the frequency of PBMC subsets determined through PCA and standard analysis.

| Subset | PCA analysis | Standard analysis |
|---|---|---|
| CD3+ CD4+ | 24.3% | 23.7% |
| CD3+ CD8+ | 31.1% | 29.5% |
| CD3− | 8.7% | 12.0% |
| CD14+ | 16.5% | 17.6% |

REFERENCES

1. Di-Yuan Tzeng et. al. Munsell Color Science Laboratory, NY 14623-5604, *A Review of Principal Component Analysis and Its Applications to Color Technology*. Color Research & Application Volume 30, Issue 2, pages 84-98, April 2005
2. Roederer M. Vaccine Research Center, NIH, Bethesda, Md. 20892-3015, USA. *Spectral compensation for flow cytometry: visualization artifacts, limitations, and caveats*. Cytometry. 2001 Nov. 1; 45(3):194-205.
3. Dennis T. Sasaki, Holden Maecker, Joe Trotter. *Establishing Optimum Baseline PMT Gains to Maximize Resolution on BD Biosciences Digital Flow Cytometers*. BD Application Note, 2005
4. Watson D A, Brown L O, Gaskill D F, Naivar M, Graves S W, Doorn S K, Nolan J P. A flow cytometer for the measurement of Raman spectra. Cytometry A. 2008 February; 73(2):119-28.
5. J. Paul Robinson. *Multispectral Cytometry: The Next Generation*. Biophotonics International, October 2004, 36-40
6. Roederer M, Hardy R R. Vaccine Research Center, NIH, Bethesda, Md. 20892-3015, USA. *Frequency difference gating: a multivariate method for identifying subsets that differ between samples*. Cytometry. 2001 Sep. 1; 45(1): 56-64.

The invention claimed is:

1. Flow cytometric system for acquiring, storing and analyzing discontinuous emission spectra data from particles, comprising:
   a light source providing an illumination beam,
   a flow cell having a detection region in which the illumination beam illuminates the passing particles within the detection region, the particles emitting an emission spectra of fluorescent light upon illumination from the illumination beam,
   two to ten optical bandpass filters which divide the emission spectra of fluorescent light from the particles almost gaplessly into at least two and up to ten separate wavelength bands,
   light detectors which receive the divided emission spectra from the optical bandpass filters, and
   a data processor programmed to:

process the discontinuous emission spectra data acquired from the fluorescent light emitted by the particles passed through said flow cell, and analyze the discontinuous emission spectra data of the at least two and up to ten separate wavelength bands divided by the optical bandpass filters via a multivariate statistic model; and wherein the optical bandpass filters are positioned between the flow cell and the light detectors.

2. The system according to claim 1, wherein the multivariate statistic model comprises multivariate analysis of variance, multivariate regression analysis, factor analysis, canonical correlation analysis, redundancy analysis, correspondence analysis, multidimensional scaling, discriminant function, linear discriminant analysis, clustering systems, recursive partitioning, principal component analysis, non-linear principle component analysis, information preserving component analysis (IPCA) and/or artificial neural networks.

3. The system according to claim 2, wherein when the multivariate statistic model comprises an information preserving component analysis (IPCA) and/or artificial neural networks, said IPCA and/or artificial neural networks comprise a principal component analysis and/or non-linear principle component analysis.

4. The system according to claim 1, wherein the data processor is programmed to analyze emission spectra data of 3, 4, 5, 6, 7, 8, 9 or 10 separate wavelength bands divided by said optical bandpass filters.

5. The system according to claim 1, wherein the data processor comprises a computational program and the program analyzes a biological particle by executing the multivariate statistic model.

6. The system of claim 5, wherein the multivariate statistic model is a principal component analysis (PCA).

7. The system according to claim 1, wherein the light source is a laser or LED.

8. The system of claim 1, comprising 4, 5, 6, 7, 8, 9 or 10 of said bandpass filters.

9. The system according to claim 1, wherein the light detectors comprise forward and side scatter detectors.

10. The system according to claim 1, wherein the wavelength bands divided by the optical bandpass filters exhibit a width of 30 to 50 nm.

11. The system according to claim 1, wherein the system is configured to receive at least two types of fluorescent particles, and the optical bandpass filters divide the emission spectrum of the at least two types of fluorescent particles almost gaplessly into at least two and up to ten separate wavelength bands such that the emission spectrum of each type of the fluorescent particles is detected within at least two different wavelength bands.

12. Flow cytometrical method comprising:
providing the system according to claim 1 and
performing flow cytometry.

13. Kit for analyzing biological particles by flow cytometry, wherein the kit comprises a system according to claim 1 and instructions for using the same.

* * * * *